US012661017B2

(12) United States Patent
Krieg

(10) Patent No.: US 12,661,017 B2
(45) Date of Patent: Jun. 23, 2026

(54) METHOD FOR OPERATING A HEARING DEVICE SYSTEM AND HEARING DEVICE SYSTEM

(71) Applicant: Sivantos Pte. Ltd., Singapore (SG)

(72) Inventor: Julius Krieg, Erlangen (DE)

(73) Assignee: Sivantos Pte. Ltd., Singapore (SG)

( * ) Notice: Subject to any disclaimer, the term of this patent is extended or adjusted under 35 U.S.C. 154(b) by 91 days.

(21) Appl. No.: 18/632,483

(22) Filed: Apr. 11, 2024

(65) Prior Publication Data

US 2025/0318735 A1    Oct. 16, 2025

(51) Int. Cl.
*A61B 5/0205* (2006.01)
*A61B 5/00* (2006.01)
*A61B 5/024* (2006.01)
*G10L 17/02* (2013.01)
*H04R 25/00* (2006.01)

(52) U.S. Cl.
CPC .......... *A61B 5/0205* (2013.01); *A61B 5/4803* (2013.01); *A61B 5/6817* (2013.01); *G10L 17/02* (2013.01); *A61B 5/02438* (2013.01); *H04R 25/604* (2013.01); *H04R 25/609* (2019.05)

(58) Field of Classification Search
CPC . A61B 5/0205; A61B 5/4803; A61B 5/02438; H04R 25/604
USPC ..................................... 381/312, 328, 23.1, 1
See application file for complete search history.

(56) References Cited

U.S. PATENT DOCUMENTS

2017/0243582 A1*  8/2017  Menezes ............. G10L 13/0335
2023/0240560 A1*  8/2023  Stumpf ................ A61B 5/6815
600/559

* cited by examiner

*Primary Examiner* — Thjuan K Addy
(74) *Attorney, Agent, or Firm* — Laurence A. Greenberg; Werner H. Stemer; Ralph E. Locher

(57) ABSTRACT

A method operates a hearing device system which has a hearing device with a microphone and a further sensor for measuring a value characterizing the heart rate of a user. The value characterizing the heart rate of the user is measured by the further sensor. A first audio signal based on an ambient sound is produced by of the microphone. The voice of the user is identified in the first audio signal and a second audio signal is produced on the basis thereof. The second audio signal is divided up into a plurality of segments depending on the characterizing value. A hearing device system is provided for operating the method.

10 Claims, 2 Drawing Sheets

METHOD FOR OPERATING A HEARING DEVICE SYSTEM AND HEARING DEVICE SYSTEM

FIELD AND BACKGROUND OF THE INVENTION

The invention relates to a method for operating a hearing device system, and a hearing device system.

Persons who suffer from a reduction in hearing ability normally use a hearing aid, which is a hearing device. Here, an ambient sound is usually converted into an electrical (audio/sound) signal by means of a microphone, i.e. an electromechanical sound transducer. The electrical signals are processed by means of a signal processing unit and are fed into the auditory canal of the person by means of a further electromechanical transducer in the form of a receiver. The signal processing unit is a component of a control unit of the hearing aid. The sound signals are furthermore mostly processed, for which purpose a signal processor of the signal processing unit is normally used. The amplification is attuned here to any loss of hearing of the hearing aid wearer.

Users of hearing aids, who are also referred to as hearing aid wearers, hearing device wearers, wearers or simply users, furthermore in most cases also have further medical conditions, as a result of which it is desirable to check their health. A corresponding measuring device, for example, is applied in order to check the health of the user. An additional activity is therefore required on the part of the user, as a result of which convenience is reduced. It is also possible for the user to forget to apply the measuring device, so that no measured values are available. It therefore becomes more difficult to analyze changes in health over time and therefore also to establish a diagnosis. Furthermore, it is not possible in this way to record the corresponding measured values essentially continuously or comparatively often.

One option is to use the existing hearing device additionally in order to determine the state of health. No additional activity is then required on the part of the user, as a result of which convenience is increased. However, the disadvantage here is that further sensors must be installed in the hearing device, which is intended to be comparatively compact and to which restrictions apply in terms of energy supply. However, it is also possible to ascertain the state of health at least partially from the voice of the user. No additional sensor is required here, since the microphone of the hearing aid can be used for this purpose. However, the evaluation requires comparatively intensive processing, so that it cannot usually be carried out by means of the hearing device itself. To overcome this, it is possible, for example, to record the ambient sound by means of the hearing device as an audio signal and then transmit this audio signal to an external server by means of which the corresponding analysis of the audio signal is carried out based on the voice and any biomarkers present therein, by means of which the state of health can be ascertained. However, the volume of data to be transmitted here is comparatively large, as a result of which the energy requirement is likewise increased. Alternatively, for example, the audio signal is compressed, wherein information can be lost due to the compression. Accuracy in determining the state of health is thus impaired.

SUMMARY OF THE INVENTION

The object of the invention is to indicate a particularly suitable method for operating a hearing device system, and a particularly suitable hearing device system, wherein, in particular, functionality is increased and the resource requirement is reduced.

This object is achieved according to the invention in terms of the method by the features of the independent method claim, and in terms of the hearing device system by the features of the independent hearing device system claim. Advantageous developments and embodiments form the subject-matter of the respective dependent claims.

The method serves to operate a hearing device system which has a hearing device. The hearing device is provided and configured to be worn on the human body. In other words, the hearing device is worn in its intended state by a wearer, who is also referred to as a user, hearing device user or hearing device wearer. The hearing device preferably comprises a retaining device, by means of which it can be attached to the human body.

The hearing device is or comprises, for example, a headphone. This is designed, for example, as an in-ear, on-ear and over-ear headphone. The headphone serves, for example, to reproduce information and/or music, and/or the headphone serves to suppress interfering noise and is referred to as a noise cancelling headphone. However, the hearing device is, in particular, a hearing aid. The hearing aid serves to support a person suffering from reduced hearing ability. In other words, the hearing aid is a medical device by means of which, for example, a partial loss of hearing is compensated. The hearing aid is, for example a "receiver-in-the-canal" (RIC) hearing aid, an "in-the-ear" hearing aid, such as an "in-the-canal" (ITC) hearing aid or a "complete-in-canal" (CIC) hearing aid. Alternatively, the hearing aid is a "behind-the-ear" hearing aid, which is worn behind an earlobe. If the hearing device is a hearing aid, it is provided and configured, for example, to be disposed behind the assigned ear or inside an auditory canal of the ear.

The hearing device comprises a microphone which serves to capture sound. In particular, an ambient sound, or at least a part thereof, is captured during operation by means of the microphone. The microphone is, in particular, an electromechanical sound transducer. The microphone has, for example, only one single microphone unit or a plurality of microphone units which interact with one another. Each of the microphone units appropriately has a membrane which is caused to vibrate by sound waves, wherein the vibrations are converted into an electrical (audio) signal by means of a corresponding recording device, such as a magnet which is moved in a coil. It is thus possible, by means of the respective microphone unit, to capture an audio signal which is based on the sound striking the microphone unit. The microphone units are designed, in particular, as unidirectional. The microphone is appropriately disposed at least partially inside a housing of the hearing device and is therefore at least partially protected.

The hearing device appropriately comprises a signal processing unit which is preferably coupled to the microphone. The signal processing unit forms, for example, a control unit of the hearing device or is appropriately a part thereof. The signal processing unit serves, in particular, to further process or at least analyze the (first) audio signal(s) produced by means of the microphone. In particular, the first audio signal is processed by means of the signal processing unit so that an output signal is produced which is modified in comparison with the first audio signal. In particular, specific frequencies of the first audio signal are amplified by means of the signal processing unit, wherein an adaptation to any loss of hearing of the wearer is preferably performed. The signal processing unit has, for example, a plurality of analog components. The signal processing unit or at least the control unit appropriately comprises a digital sound processor (DSP). The (sound) processor is appropriately designed as programmable.

The hearing device preferably has a receiver which serves, in particular, to output the respective output signal. Here, the output signal is, in particular, an electrical signal. The receiver is appropriately coupled to the signal processing unit, in particular has a signaling connection thereto. Depending on the design of the hearing device, the output device is disposed, in the intended state, at least partially inside an auditory canal of the wearer of the hearing device, i.e. a person, and is at least acoustically connected thereto.

In particular, the hearing device is wireless and is provided and configured to be inserted at least partially into an auditory canal. The hearing device particularly preferably comprises an energy storage device by means of which an energy supply is provided. The hearing device preferably has a communication device which comprises, in particular, a radio system. The first audio signal is received, and therefore made available, for example, during operation by means of the communication device.

Moreover, the hearing device system has a further sensor. The further sensor is separated, for example, from the microphone or is disposed, for example, adjacent to it. The further sensor is, for example, a component of the hearing device. In one alternative, the further sensor is a component of a further device of the hearing device system. In particular, the hearing device system comprises only the hearing device. Alternatively, the hearing device system comprises the further device to which, for example, the further sensor is assigned. The further sensor is suitable for measuring a value characterizing the heart rate of the user, and is provided and configured, in particular, for this purpose. The further sensor therefore suitably serves to measure the value which characterizes the heart rate and which is also referred to below simply as the value. The further sensor is, in particular, a cardiovascular sensor.

The further sensor comprises, in particular, one or more sensor units or is formed by means of only one single sensor unit. Here, the sensor unit is, for example, a blood oxygen sensor, for example a photoplethysmography sensor (PPG sensor). Oxygen saturation changes periodically with each pulse beat, so that the heart rate can be determined on the basis thereof. Alternatively, an electrocardiogramsor (ECG sensor) is used as the sensor unit. The heartbeat, and therefore the heart rate, are therefore determined electrically, in particular on the basis of an applied electrical voltage/potential. Alternatively, the sensor unit is an acceleration sensor. In particular, the movement of an artery due to the pulse beat, resulting in a movement of the overlying tissue and therefore the sensor unit also, is determined by means of the acceleration sensor. The acceleration sensor is, for example, a vibrometer/vibration meter, which is designed, for example, as MEMS-based or as a laser Doppler vibration meter. Alternatively, the sensor unit is designed as a seismocardiography sensor (SCG) or a phonocardiography sensor (PCG).

The further sensor is formed, for example, by means of one of these sensor units. In other words, one of the sensor units forms the further sensor. Alternatively, the further sensor comprises a plurality of sensor units which are, for example, of identical design but are arranged at different positions. Alternatively, at least two or all of the sensor units of the further sensor differ from one another. A comparatively differentiated determination of the characterizing value is thus enabled.

The method provides that the value characterizing the heart rate of the user is measured by means of the further sensor. In particular, continuous measured values, i.e. a time sequence corresponding to the value, are recorded for this purpose. The heart rate, for example, is derivable from the value. In particular, the value or a characteristic of the value is essentially repeated periodically with the heart rate. The change in the pulse beats over time, for example, the beats of the heart or of the electrical excitation of the heart is/are used as the value. The characterizing value is, for example, the oxygen saturation of the blood, an electrocardiogramal, an electrical voltage, a movement of an artery or a seismocardiography or phonocardiography signal.

A first audio signal is produced by means of the microphone. This is based on the ambient sound and preferably corresponds to the recorded ambient sound. Alternatively, the ambient sound is furthermore processed, for example filtered. Particularly preferably, however, the first audio signal is essentially the unprocessed electrical signal provided by means of the microphone.

The voice of the user is identified in the first audio signal. If the voice is not present and cannot therefore be identified, the method is, in particular, interrupted, or the first audio signal is produced until the voice can be identified. A frequency analysis, for example, is carried out, or this is performed by means of a neural network, in order to identify the voice. The hearing device preferably comprises an "own voice detector" which is used to identify the voice. A second audio signal is produced on the basis of the identified voice. In other words, the second audio signal is produced depending on the voice.

The second audio signal is divided up into a plurality of segments depending on the value. The second audio signal is divided up here, for example, with each occurrence of a heartbeat/pulse beat so that the number of segments corresponds to the number of heartbeats during the second audio signal. In particular, a heartbeat/pulse beat is therefore assigned in each case to each of the segments.

On the basis of the method, it is therefore possible to further process only the individual segments in order to ascertain the state of health of the user. The volume of data to be processed is therefore reduced so that, for example, no compression is required. Accuracy in determining the state of health is thus increased, wherein the resource requirement is not increased. Due to the segmentation, the individual segments can be transmitted separately/successively, as a result of which the required bandwidth is reduced. An analysis can also be carried out even before all segments are present. Since the division is performed depending on the characterizing value, the influence of the heartbeat/heart rate is always the same for each segment, as a result of which the individual segments are comparable with one another. A complex post-processing or the like is at least not required. A knowledge of the characterizing value is no longer required during a subsequent evaluation/analysis of the segments, since the segments are already comparable with one another. Complexity is therefore reduced. The analysis is suitably performed by means of microprosody.

The hearing device system has, for example, only the hearing device. Alternatively, the hearing device system comprises two hearing devices of this type, so that the hearing device system is designed as binaural. The two hearing devices preferably have a signaling connection to one another, for example by means of Bluetooth. The microphone, for example, is assigned to one of the hearing devices, and the further sensor is assigned to the other hearing device. Alternatively, the two hearing devices are of identical design or in each case have at least the further sensor.

The characterizing value is measured, for example, essentially continuously by means of the further sensor. The latter is further used, for example, in other analyses. The first audio signal is preferably always produced by means of the microphone and the voice of the user is identified therein. Alternatively, the identification (or at least the attempted identification) of the voice is carried out only if the characterizing value has a specific property.

However, the first audio signal is particularly preferably produced essentially continuously by means of the microphone and the voice is identified therein. The first audio signal is appropriately processed here by means of the possibly provided signal processing unit and/or at least the possibly provided output signal is produced on the basis of the first audio signal and is fed to the possibly provided headphone. The further sensor is appropriately operated only if the voice is identified, so that the value characterizing the heart rate of the user is measured. The energy requirement is thus reduced.

The segments are further processed, for example, in the same way and are, for example, not further differentiable. However, a timestamp is preferably determined for each segment and, in particular, is assigned to said segment. Here, the timestamp is, for example, absolute, such as a clock time. Alternatively, the timestamp is relative, and the position in the respective second audio signal is suitably described by means thereof. Alternatively, a counter is used as a timestamp, wherein the number 1, for example, is assigned to the first created segment, the number 2 is assigned to the second segment, etc. In this way, it is identifiable when, for example, an artefact present in one of the segments occurred and/or it is possible, for example, to exclude specific segments for a subsequent analysis, for example because specific environmental influences prevailed, as a result of which the second audio signal is corrupted. An evaluation of a change in the state of health is also enabled due to the timestamp.

The segments, for example, are not further processed. However, the lengths of the segments are particularly preferably matched to one another. If the heart rate thus changes, the characterizing value changes and therefore also, for example, the length of the segments. Comparability is nevertheless achieved by matching the lengths to one another, and a subsequent analysis is therefore simplified. Here, for example, the length to which the segments are matched is predefined externally. Alternatively, the length that is applied for the matching corresponds, for example, to the length of the longest or shortest of the segments into which the second audio signal is divided up. In summary, the segments are, in particular, scaled.

The part of the first audio signal, for example, which comprises or is formed from the voice is used as the second audio signal. Complexity is therefore reduced. However, a vowel is particularly preferably identified in the identified voice, and this part of the identified voice is appropriately used as the second audio signal. The volume of data to be processed is therefore reduced. Corresponding vowels also occur comparatively often, so that the state of health of the user can be analyzed comparatively frequently. Each vowel, for example, is used here, or only specific vowels, preferably the "a". The analysis is simplified with his vowel. This vowel is furthermore essentially always pronounced in the same way.

Alternatively, a keyword is monitored, for example, in the identified voice, i.e. to detect whether a keyword is present. The keyword is then used as the second audio signal. An increased length is therefore present, thus improving the meaningfulness of the analysis. The number of segments is increased due to the use of the keyword, so that the analysis is improved. The keyword is essentially always pronounced in the same way, thus achieving comparability of segments from different second audio signals. Alternatively, the user is prompted, for example, to speak a specific word or a specific sentence. This part of the voice is then used as the second audio signal. It is thus ensured that the user always uses the same/desired intonation, thereby further increasing comparability.

The segments are, for example, further processed/analyzed directly by means of the hearing device or the hearing device system. However, a data set is particularly preferably created on the basis of the segments and is stored. A subsequent analysis is therefore possible. The state of health of the user is ascertainable from the data set, wherein this can be performed, for example, retrospectively. In particular, the data set is stored in a memory of the hearing device system, for example in a memory of the hearing device. Alternatively, the data set is stored, for example, in a memory of the possibly provided further device of the hearing device system which is, for example, a smartphone or a smartwatch. A comparatively large memory and a comparatively large energy store are therefore available, so that an operation of the hearing device is not impaired, wherein the structural size of the hearing device is not increased.

The mean value of the segments, for example, is created and assigned to the data set. Any existing artefacts are essentially averaged out due to the mean value formation, so that, for example, existing effects are systematically determinable in a comparatively precise manner. These effects always occur, in particular, at the same position within the segments. In particular, the length of the segments is initially adapted here so that the mean value formation is simplified. The evaluation is preferably carried out by means of microprosody.

The mean value is formed, for example, by means of the segments which are created from the same second audio signal. Alternatively, the mean value is formed from segments which were created from different second audio signals. A plurality or only one single segment, for example, is used here from each second audio signal. In this way, artefacts present due to the heartbeat are reduced so that, for example, other symptoms or the like are ascertainable, on the basis of which the state of health of the user can again be determined. Parkinson's disease, in particular, is diagnosable with a mean value formation of this type.

The data set is formed, for example, by means of the mean value alone, so that only a comparatively small memory is required, as a result of which hardware resources are reduced. The data set is formed, for example, by means of the mean value alone. Alternatively, for example, the segments are assigned directly to the data set. The respective timestamp is preferably determined for each of the segments and the segments are likewise appropriately assigned to the data set. A comparatively comprehensive analysis of the state of health of the user is therefore then possible, even over a comparatively long period of time and in a differentiated manner. Both the segments and the mean value are particularly preferably assigned to the data set. Different analyses can therefore subsequently be performed, wherein flexibility in the performance is increased, and wherein excessive calculations are no longer required.

Alternatively or in combination therewith, a feature is determined for each segment and is assigned to the data set. The feature here is, for example, the maximum of the prevailing sound pressure, the variability of the frequency, or the prevalence of a specific characteristic. The feature is appropriately determined in the same way for each segment, so that comparability is achieved. Each feature preferably comprises different characteristics, so that a following analysis is simplified. Due to the use of the features, a required volume of data is further reduced, as a result of which, in particular, the required size of the memory is further reduced. A transmission of the data set with small bandwidths, for example, is also subsequently possible. Alternatively, for example, the mean value and/or the segments are further assigned to the data set. Different subsequent analyses are therefore possible, wherein complexity is reduced.

The value, i.e., in particular, the change in the measured value over time, which is produced by means of the further sensor, is preferably assigned to the data set. This value is stored, for example, continuously in the data set, or preferably for each segment. In other words, the corresponding part of the value is assigned to each segment. A further analysis, for example, can therefore be performed on the basis thereof.

A subsequent analysis of the segments, preferably of the possibly provided data set, is performed, for example, by means of the hearing device system. A classification is performed, for example, or a neural network is used for this purpose. A stiffness of arteries, for example, is determined by means of the segments, on the basis of which, for example, a heart attack or a stroke or at least in each case a risk thereof can be determined. Alternatively or in combination therewith, for example, an ejection fraction, a heart contractility, a blood pressure, a heart rate, a variability in the heart rate, a respiration rate, a pulse wave velocity or a variability thereof is determined. Microprosody is appropriately used here, and, in particular, a jitter or a shimmer. The hearing device system particularly preferably comprises a wearable, for example a smartphone or a smartwatch, on which an app is executed. The method is carried out, in particular, depending on an activation of the app.

The hearing device system has a hearing device with a microphone, which is designed, in particular, as a hearing aid. The hearing device system further comprises a further sensor which is, for example, a component of the hearing device or of a further device separated therefrom, for example a wearable. The further sensor serves to measure a value characterizing the heart rate of a user and is suitable and appropriately provided and configured for this purpose.

The hearing device system is operated according to a method in which the value characterizing the heart rate of the user is measured by means of the further sensor. A first audio signal is produced by means of the microphone on the basis of an ambient sound, and the voice of the user is identified in the first audio signal and a second audio signal is produced on the basis thereof. The second audio signal is divided up into a plurality of segments depending on the characterizing value. The method is at least partially carried out in a suitable manner by means of a signal processing unit/control unit which is suitable and, in particular, provided and configured for this purpose. The signal processing unit/control unit is, in particular, a component of the hearing device. The hearing device system appropriately further comprises a smartphone/smartwatch which, at least when the method is carried out, has a signaling connection to the hearing device.

The developments and advantages described in connection with the method can also be transferred accordingly to the hearing device system, and vice versa.

Matching parts are denoted in all figures with the same reference signs.

DETAILED DESCRIPTION OF THE INVENTION

Figure 1:
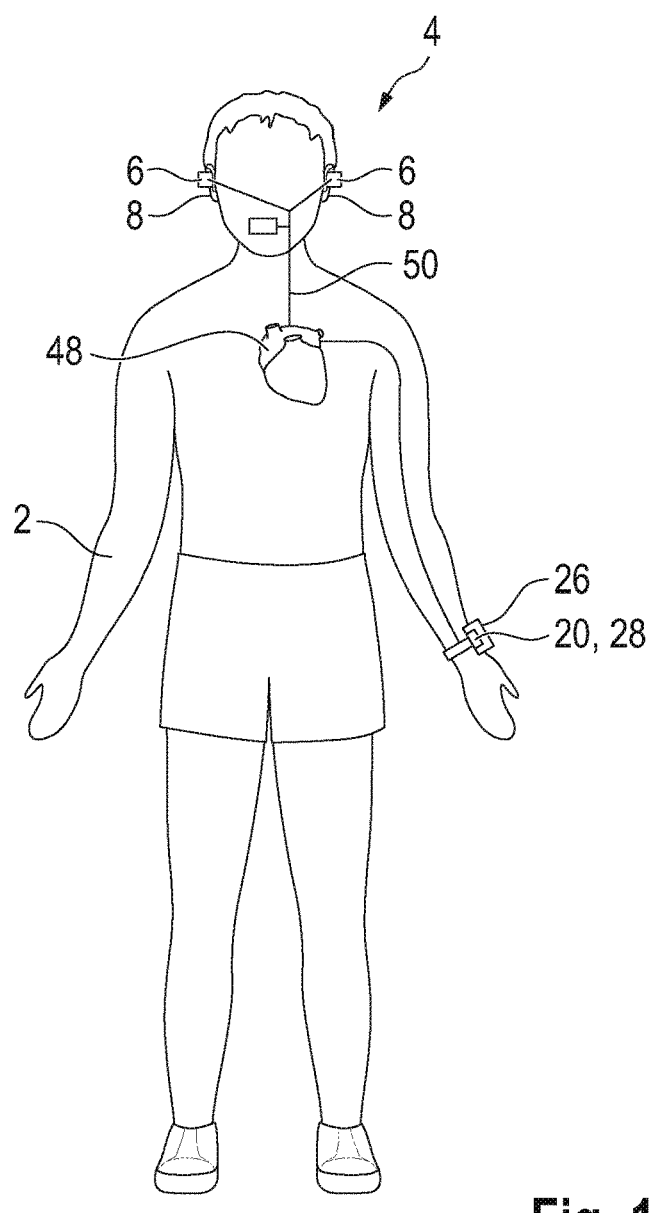
FIG. 1 shows schematically a user who is wearing a hearing device system having two hearing devices.

FIG. 1 shows a schematically simplified view of a user 2 who is wearing a hearing device system 4. The hearing device system 4 has two hearing devices 6 which are designed as mirror images of one another and are assigned to different ears 8 of the user 2.

Figure 2:
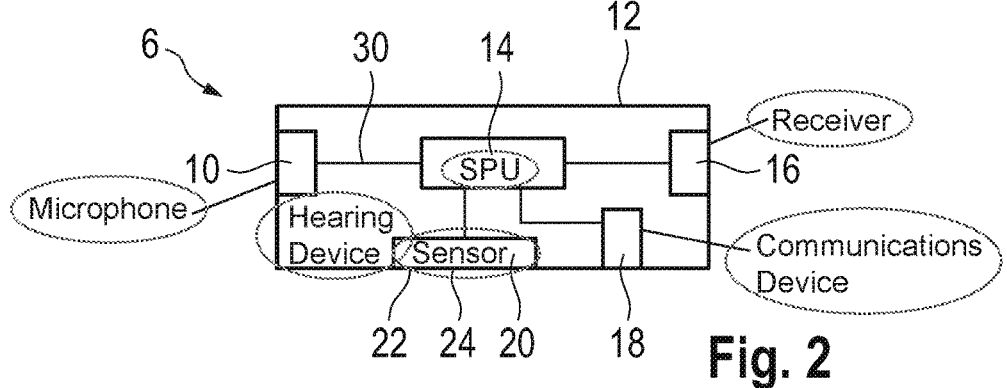
FIG. 2 shows schematically one of the hearing devices which comprises a microphone.

FIG. 2 shows a schematically simplified view of one of the hearing devices 6 which, when worn, is located at least partially in the assigned auditory canal of the user 2. The hearing device 6 has a microphone 10 which is disposed inside a housing 12 and has a signaling connection to a signal processing unit 14 which is similarly disposed in the housing 12 and also forms the control unit of the hearing device 6. The signal processing unit 14 is connected to a receiver 16 which represents the internal termination of the hearing device 6 in the assigned ear 8.

The hearing device 6 further comprises a communication device 18 which operates according to the Bluetooth standard and provides the signaling interconnection between the individual components of the hearing device system 4. The hearing device 6 also has a further sensor 20 which comprises an acceleration sensor 22, i.e. a MEMS-based accelerometer. The further sensor 20 further comprises an electrocardiography sensor 24. In summary, the electrocardiography sensor 24 and the acceleration sensor 22 are used as the further sensor 20.

The hearing device system 4 further has a further device 26, i.e. a wearable. In the case shown, this is designed as a smartwatch and similarly has the further sensor 20 and the communication device (not shown in detail). In the case of the further device 26, the further sensor 20 is designed as an oxygen sensor 28. In other words, the blood oxygen sensor 28 is used as the further sensor 20.

In normal operation, ambient sound is captured by means of the microphone 10 and a first audio signal 30 is produced on the basis thereof and is fed to the signal processing unit 14. Processing is carried out there depending on a loss of hearing of the user 2. The first audio signal 30 processed in this way is fed as an output signal to the receiver 16 and is output by means of the receiver 16 into the assigned ear 8 of the user 2. The processing is further carried out, for example, using data exchanged by means of the communication device 18 between the different hearing devices 6.

Figure 3:
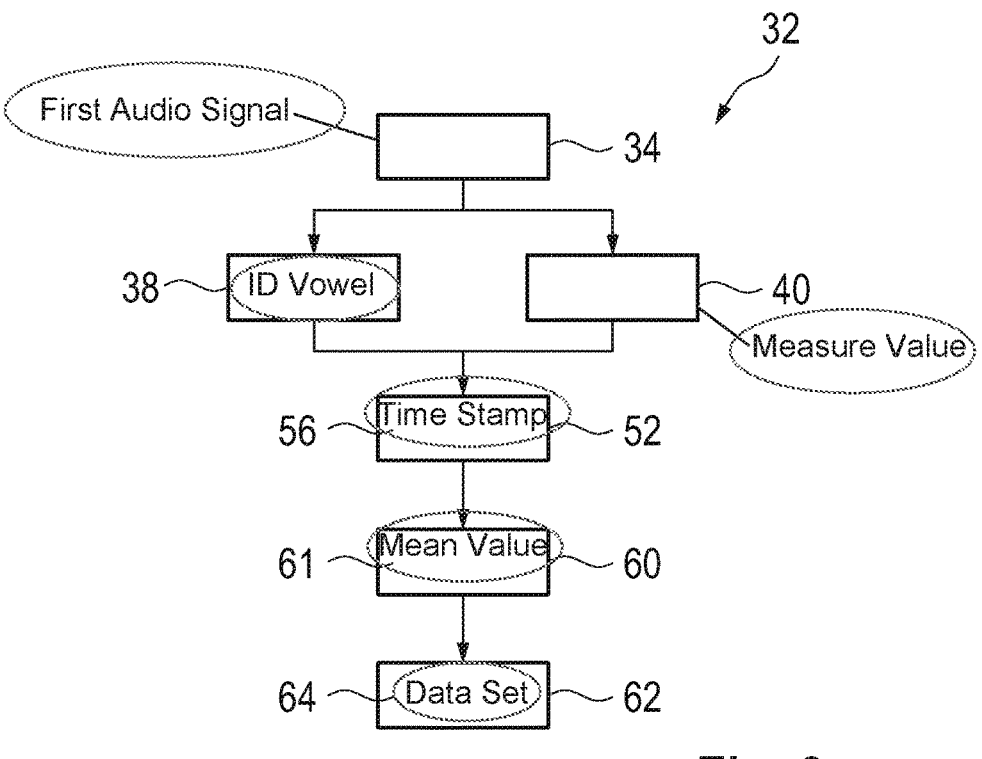
FIG. 3 shows a method for operating the hearing device system.

FIG. 3 shows a method 32 for operating the hearing device system 4, said method being carried out at least partially by means of the signal processing unit adapted thereto. In summary, the hearing device system 4 is operated according to the method 30.

Figure 4:
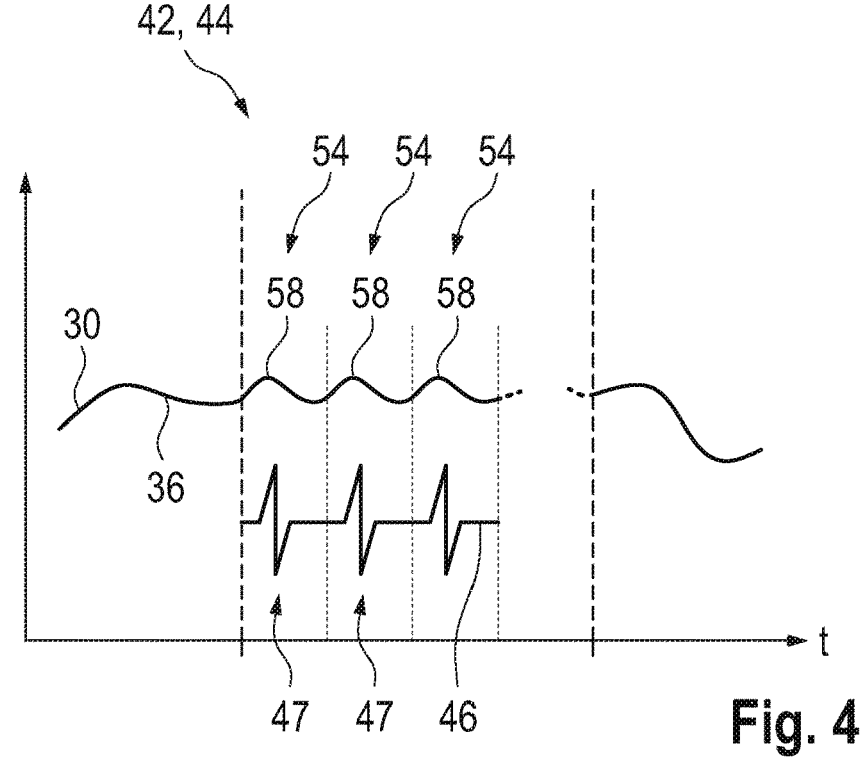
FIG. 4 shows the change over time of an audio signal captured by means of the microphone.

In a first work step 34, the first audio signal 30 based on the ambient sound is produced by means of the microphone 10. The voice 36 of the user 2 is further identified in the first audio signal 30, of which the change over time is shown in FIG. 4, for which purpose a suitable filter is used. In the example shown, the first audio signal 30 corresponds to the voice 36, so that no additional signal components are present. If the voice 36 of the user 2 has been identified, a second work step 38 and a third work step 40 are then carried out essentially simultaneously. The first work step 34 is carried out until the voice 36 is identified.

In the second work step 38, a vowel 42, i.e. the "A", is identified in the identified voice 36, and this part is used as a second audio signal 44. The second audio signal 44 thus corresponds to ambient sound which has occurred due to the utterance of the user 2, i.e. the "A". In summary, the first audio signal 30 is thus produced by means of the micro-phone 10 on the basis of the ambient sound, and the voice 36 of the user 2 is identified in the first audio signal 30. The second audio signal 42 is produced on the basis thereof, i.e. by identifying the vowel 42 in the identified voice 36. This is then used as the second audio signal 44. The end of the utterance of the vowel 42 and therefore of the second audio signal 44 also defines the end of the second work step 38.

In the third work step 40 carried out temporally in parallel, a value 46 characterizing the heart rate of the user 2 is measured by means of the further sensor 20. In other words, the frequency of occurrence of a heartbeat 47 is stored, at least implicitly, in the value 46. When the heart 48 of the user 2 beats, blood is pumped rhythmically through the arteries 50 thereof. Consequently, the blood oxygen concentration similarly changes at the same frequency, so that the value 46 characterizing the heart rate of the user 2 is measured by means of the oxygen sensor 28. Due to the rhythmic pumping, the dilation of the arteries 50 also changes and this is measured by means of the acceleration sensor 22 insofar as the latter is applied directly to the skin of the user. The value 46 characterizing the heart rate of the user 2 is therefore also measured by means of the accelera-tion sensor 22. The electrical voltage which occurs due to the beating of the heart 48 and which changes periodically is also measured by means of the electrocardiography sensor 24. The value 46 which characterizes the heart rate is therefore also measured by means of the electrocardiogra-phy sensor 24.

In summary, the value 46 characterizing the heart rate is measured by means of the further sensors 20, said value 46 having a different characteristic according to the configura-tion of the further sensor 20, wherein, however, the charac-teristic is repeated periodically with the heart rate. FIG. 4 shows by way of example the value 46 determined by means of the electrocardiography sensor 24. In summary, the further sensors 20 serve to measure the value 46 character-izing the heart rate of the user 2, wherein the value 46 has different properties depending on the further sensor 20 that is used.

In a following fourth work step 52, the second audio signal 44 is divided up into a plurality of segments 54 depending on the characterizing value 46. One of the heart-beats 47 is assigned here in each case to each of the segments 54, and if the heart 48 performs a specific movement, one of the segments 54, in particular, begins. The previous segment 54 ends, for example, at the beginning or at the end of each heartbeat 47, and the following segment 54 is started. A timestamp 56 which is, for example, absolute, i.e. the current clock time at which the respective segment 54 began, is determined here for each segment 54. In summary, the second audio signal 44 is thus divided up into the individual segments 54. This is carried out depending on the heartbeats 47 which occur, wherein the heartbeats 47 are stored by means of the value 46. A feature 58 is further determined for each of the segments 54, i.e., in the example shown, where the maximum of the respective segment 54 is in each case located.

In a subsequent fifth work step 60, the lengths of the segments 54 are matched to one another. If the heart rate is constant, the length of the segments 54 is identical, since said segments are created depending on the heart rate. However, if the heart rate changes, the length of the seg-ments 54 also changes. This is equalized so that a scaling is carried out. All segments 54 subsequently have the same length. The mean value 61 of the segments 54 is then formed, for which purpose the segments 54 are added together and the result is divided by the number of segments 54.

A data set 64 is created in a subsequent sixth work step 62. The mean value 61 of the segments 54 and the segments 54 themselves are assigned to this data set 64. The timestamps 56 and the features 58 are also assigned to the data set 64. The data set 64 is thus created on the basis of the segments 54. The value 46 is also assigned to the data set 64.

The data set 64 is further stored in a memory (not shown in detail) of the hearing device 6 or of the further device 26. An analysis of the data set 64 and therefore, at least implicitly, of the voice 36 of the user 2 for the presence of illnesses or the like is thus enabled. In other words, the voice 36 can be used for the subsequent analysis and for deter-mining biomarkers, wherein the required storage is reduced. Compression is not required here.

The invention is not limited to the exemplary embodiment described above. On the contrary, other variants of the invention can also be derived therefrom by a person skilled in the art without departing the subject-matter of the inven-tion. In particular, all individual features described in con-nection with the exemplary embodiment are furthermore also combinable with one another in other ways without departing the subject-matter of the invention.

REFERENCE SIGN LIST

2 User
4 Hearing device system
6 Hearing device
8 Ear
10 Microphone
12 Housing
14 Signal processing unit
16 Receiver
18 Communication device
20 Further sensor
22 Acceleration sensor
24 Electrocardiography sensor
26 Further device
28 Oxygen sensor
30 First audio signal
32 Method
34 First work step
36 Voice
38 Second work step
40 Third work step
42 Vowel

44 Second audio signal
46 Value
47 Heartbeat
48 Heart
50 Artery
52 Fourth work step
54 Segment
56 Timestamp
58 Feature
60 Fifth work step
61 Mean value
62 Sixth work step
64 Data set

The invention claimed is:

1. A method for operating a hearing device system having a hearing device with a microphone and a further sensor for measuring a value characterizing a heart rate of a user, which comprises the steps of:
   measuring the value characterizing the heart rate of the user by means of the further sensor;
   producing a first audio signal based on an ambient sound by means of the microphone;
   identifying a voice of the user in the first audio signal;
   producing a second audio signal on a basis of the first audio signal;
   dividing up the second audio signal into a plurality of segments depending on the value characterizing the heart rate; and
   matching lengths of the segments to one another.

2. The method according to claim 1, which further comprises determining a timestamp for each segment of the plurality of segments.

3. The method according to claim 1, wherein during each segment therein is only one heartbeat.

4. The method according to claim 1, which further comprises identifying a vowel in the voice identified and the vowel is used as the second audio signal.

5. The method according to claim 1, which further comprises creating a data set on a basis of the segments and storing the data set.

6. The method according to claim 5, which further comprises determining a mean value of the segments and assigning the mean value to the data set.

7. The method according to claim 5, which further comprises assigning the segments to the data set.

8. The method according to claim 5, which further comprises determining a feature of each segment of the segments and assigning the feature to the data set.

9. The method according to claim 5, which further comprises assigning the value to the data set.

10. A hearing device system, comprising:
   a hearing device having a microphone and a further sensor for measuring a value characterizing a heart rate, the hearing system is programmed to:
   measure the value characterizing the heart rate of the user by means of said further sensor;
   produce a first audio signal based on an ambient sound by means of said microphone;
   identify a voice of the user in the first audio signal;
   produce a second audio signal on a basis of the first audio signal;
   divide up the second audio signal into a plurality of segments depending on the value characterizing the heart rate; and
   match lengths of the segments to one another.

* * * * *